(12) United States Patent
Ghodsian et al.

(10) Patent No.: US 8,105,308 B2
(45) Date of Patent: Jan. 31, 2012

(54) PERMANENT UMBILICAL HOLLOW TUBE

(75) Inventors: Kamran Ghodsian, Newport Beach, CA (US); Maziar Ghodsian, Newport Beach, CA (US)

(73) Assignee: Ghodsian Laboratories, Inc., Los Angeles, CA (US)

( * ) Notice: Subject to any disclaimer, the term of this patent is extended or adjusted under 35 U.S.C. 154(b) by 0 days.

(21) Appl. No.: 12/185,070

(22) Filed: Aug. 2, 2008

(65) Prior Publication Data
US 2010/0030145 A1 Feb. 4, 2010

(51) Int. Cl.
*A61M 31/00* (2006.01)

(52) U.S. Cl. .................................................. 604/500

(58) Field of Classification Search ............... 604/264, 604/278, 164.13, 167.04, 103.01, 164.02, 604/164.01, 890.1, 500; 623/23.68, 23.64; 606/194
See application file for complete search history.

(56) References Cited

U.S. PATENT DOCUMENTS

| | | | |
|---|---|---|---|
| 4,096,862 A | 6/1978 | DeLuca | |
| 4,378,016 A | 3/1983 | Loeb | |
| 4,545,367 A * | 10/1985 | Tucci | 128/898 |
| 4,567,882 A | 2/1986 | Heller | |
| 5,100,392 A | 3/1992 | Orth et al. | |
| 5,222,949 A | 6/1993 | Kaldany | |
| 5,314,471 A | 5/1994 | Brauker et al. | |
| 5,387,237 A | 2/1995 | Fournier et al. | |
| 5,843,069 A * | 12/1998 | Butler et al. | 604/891.1 |
| 6,129,668 A | 10/2000 | Haynor et al. | |
| 6,413,250 B1 * | 7/2002 | Smith | 604/533 |
| 6,551,285 B1 | 4/2003 | Bierman | |
| 7,010,338 B2 | 3/2006 | Ritter et al. | |
| 2002/0128604 A1 * | 9/2002 | Nakajima | 604/164.01 |
| 2003/0172940 A1 * | 9/2003 | Rogers et al. | 128/899 |
| 2006/0204532 A1 * | 9/2006 | John | 424/422 |

FOREIGN PATENT DOCUMENTS

WO WO81/00159 6/1981

OTHER PUBLICATIONS

T. Kiserud, S. Rasmussen; How repeat measurements affect the mean diameter of the umbilical vein and the ductus venosus; 1998; Ultrasound Obstet Gynecol; 11:419-425.*

* cited by examiner

*Primary Examiner* — Christopher D Koharski
(74) *Attorney, Agent, or Firm* — Sam K. Tahmassebi; TechLaw LLP

(57) ABSTRACT

An apparatus is provided. The apparatus includes a tube having a first end and a second end. The second end prevents access to an inner wall of the tube. Further, the apparatus includes a valve operably connected to the first end of the tube and configured to provide access to the inner wall of the tube to a guiding member inserted through the valve. The guiding member positions the tube in an umbilical vessel of an umbilical cord prior to occlusion of the umbilical vessel so that the tube remains within the umbilical vessel after occlusion of the umbilical vessel.

15 Claims, 5 Drawing Sheets

FIG. 1C
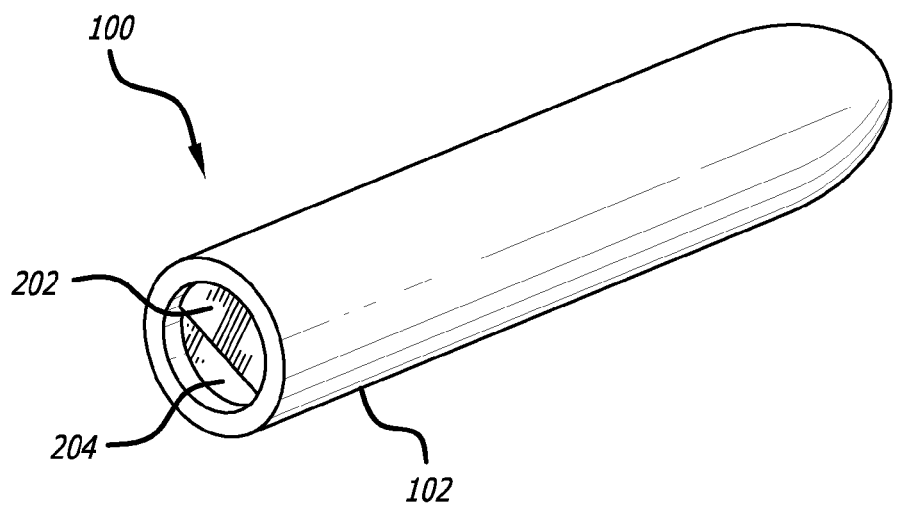
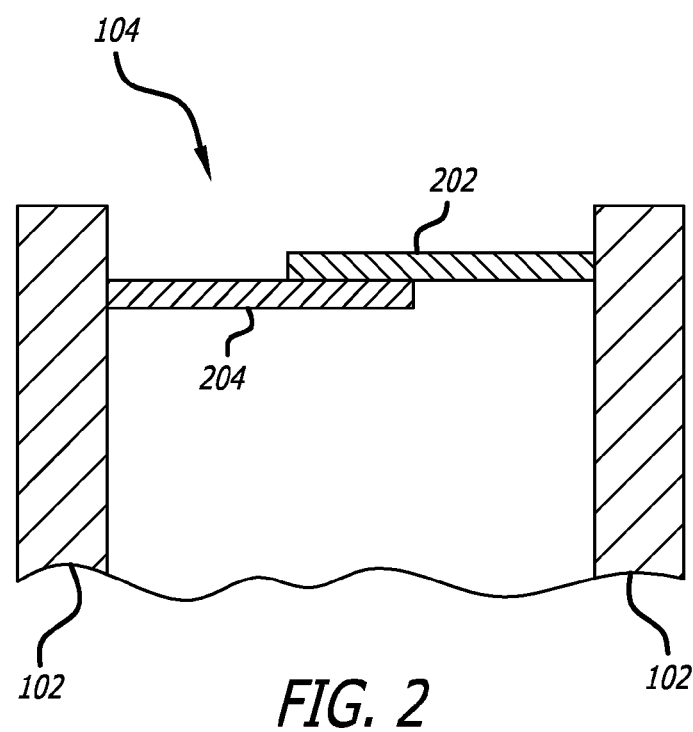
FIG. 2

PERMANENT UMBILICAL HOLLOW TUBE

BACKGROUND

1. Field

This disclosure generally relates to the field of medical devices. More particularly, the disclosure relates to an umbilical medical device.

2. General Background

The delivery or extraction of fluids, pharmaceuticals, or medicines to and from patients may at times necessitate invasive procedures. The invasive procedures may be needed to gain access to specific areas of the body. However, these invasive procedures may often involve making deep incisions underneath the skin and/or muscles of the patient. As a result, the patients may undergo a substantial amount of pain. Further, a lengthy recovery time may be needed as well as an increase risk for infection. In addition, the depth of these incisions may lead to permanent scarring of the skin and increase their susceptibility for infection. For example, an incision into the abdomen of the patient to deliver medicine may typically be at least two centimeters to three centimeters.

As a result, patients are often hesitant about undergoing such invasive procedures. Accordingly, physicians utilize these types of procedures only when necessary. Therefore, the current modes of medicinal delivery are underutilized, which leads to a less than optimal approach for diagnosis and treatment.

SUMMARY

In one aspect of the disclosure, an apparatus is provided. The apparatus includes a tube having a first end and a second end. The second end prevents access to an inner wall of the tube. Further, the apparatus includes a valve operably connected to the first end of the tube and configured to provide access to the inner wall of the tube to a guiding member inserted through the valve. The guiding member positions the tube in an umbilical vessel of an umbilical cord prior to occlusion of the umbilical vessel so that the tube remains within the umbilical vessel after occlusion of the umbilical vessel.

In another aspect of the disclosure, a process is provided. The process inserts, with a guiding member, a tube into an umbilical vessel in an umbilical cord prior to occlusion of the umbilical vessel so that the tube remains within the umbilical vessel after occlusion of the umbilical vessel. Further, the process removes the guiding member from the tube. Finally, the process clamps the umbilical cord.

In yet another aspect of the disclosure, a kit is provided. The kit includes a tube having a first end and a second end. The second end prevents access to an inner wall of the tube. Further, the kit includes a guiding member. Further, the kit includes a valve operably connected to the first end of the tube and configured to provide access to the inner wall of the tube to the guiding member inserted through the valve. Finally, the guiding member positions the tube in an umbilical vessel of an umbilical cord prior to occlusion of the umbilical vessel so that the tube remains within the umbilical vessel after occlusion of the umbilical vessel.

In another aspect of the disclosure, a process is provided. The process inserts a tube into an umbilical vessel in an umbilical cord prior to occlusion of the umbilical vessel so that the tube remains within the umbilical vessel after the occlusion of the umbilical vessel. Further, the process clamps the umbilical cord.

In yet another aspect of the disclosure, an apparatus is provided. The apparatus includes a tube having a first end and a second end, the tube being positioned in an umbilical vessel of an umbilical cord prior to occlusion of the umbilical vessel so that the tube remains within the umbilical vessel after occlusion of the umbilical vessel. The apparatus also includes a first barrier located at the first end that prevents access to an inner wall of the tube. Further, the process includes a second barrier located at the second end that prevents access to an inner wall of the tube.

In another aspect of the disclosure, an apparatus is provided. The apparatus includes a tube having a first end and a second end. The second end prevents access to an inner wall of the tube. Further, the apparatus includes a first valve operably connected to the first end of the tube and configured to provide access to the inner wall of the tube to a guiding member inserted through the first valve. The guiding member positions the tube in an umbilical vessel of an umbilical cord prior to occlusion of the umbilical vessel so that the tube remains within the umbilical vessel after occlusion of the umbilical vessel. In addition, the apparatus includes a second valve operably connected to the second end of the tube and configured to provide access to the inner wall of the tube to a guiding member inserted through the second valve.

BRIEF DESCRIPTION OF THE DRAWINGS

The above-mentioned features of the present disclosure will become more apparent with reference to the following description taken in conjunction with the accompanying drawings wherein like reference numerals denote like elements and in which:

FIG. 1C illustrates a plan view of the permanent umbilical hollow tube as shown in FIG. 1A.

FIG. 2 illustrates a magnified view of the valve.

DETAILED DESCRIPTION

A permanent umbilical hollow tube is provided. The umbilical cord is utilized to provided nourishment and oxygenation to the fetus during the fetus's development. The umbilical cord has umbilical vessels. For example, the umbilical vessels in the umbilical cord usually include one umbilical vein and two umbilical arteries. After birth, the umbilical cord is clamped after the newborn is separated from the placenta. Although temporary catheterization of the umbilical vessels may be utilized for a short time period to provide access to the newborn through the umbilical cord, the remnant of the umbilical vein and two umbilical arteries in the newborn's body will ultimately occlude when that access is discontinued. Soon after birth, postnatal closure of the umbilical arteries and the umbilical vein begins. The umbilical arteries and the umbilical vein will be completely occluded within a few days thereafter. The umbilical vein subsequently becomes the ligamentum teres hepatic, which is also called the Teres Ligament. The ligamentum teres usually measures between ten and twenty centimeters on the anterior abdominal wall extending from the umbilicus to the liver. The two umbilical arteries usually measure between fifteen centimeters to twenty five centimeters long and become the medial umbilical ligaments, which is also called the Urachus, extending from the umbilicus toward the bladder. The diameter of the two umbilical arteries is each approximately one to two millimeters. Further, the diameter of the umbilical vein is approximately three millimeters to five millimeters.

In one embodiment, the permanent umbilical hollow tube is positioned in the umbilical vein or one of the two umbilical arteries to keep the vessel within which the permanent umbilical hollow tube is positioned open. However, the ligaments will develop beyond the area that is occupied by the permanent umbilical hollow tube. During the growth of the individual, the permanent umbilical hollow tube will remain at the same position of insertion in the individual's body. As a result, the permanent umbilical hollow tube may be utilized for direct access into the body for effective diagnosis and/or delivery of medicine in an intended area without the conventional problems associated with invasive procedures, e.g., pain, scarring, infection etc. Further, in one embodiment, the positioning of the hollow tube is in the umbilical vein or one of the two umbilical arteries in the body to keep the vessel within which the permanent umbilical hollow tube is positioned open.

Figure 1A:
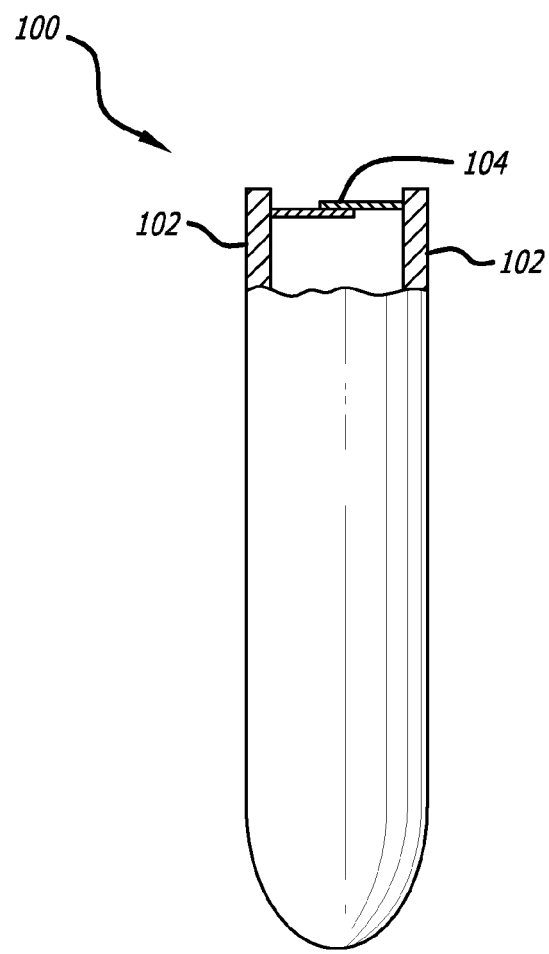
FIG. 1A illustrates a side view of a permanent umbilical hollow tube.

FIG. 1A illustrates a side view of a permanent umbilical hollow tube 100. In one embodiment, the permanent hollow tube 100 has a connector 102 that is utilized to connect a valve 104 to the permanent umbilical hollow tube 100. The valve 104 provides access to the interior of the permanent umbilical hollow tube 100 when opened and may be closed to store a variety of items such as medicine. In one embodiment, the connector 102 may extend around a portion of the interior of the permanent umbilical hollow tube 100. The connector 102 may be adhered to the inside wall of the permanent umbilical hollow tube 100 by adhesives, sutures, screws, bolts, nails or the like. Further, the connector 102 may be adhered to the valve 104 by adhesives, sutures, screws, bolts, nails or the like.

Figure 1B:
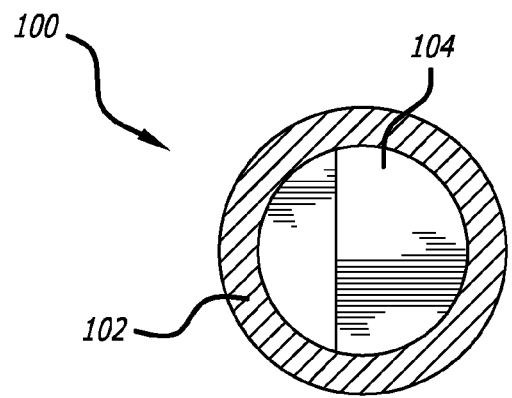
FIG. 1B illustrates a top view of the permanent umbilical hollow tube as shown in FIG. 1A.

FIG. 1B illustrates a top view of the permanent umbilical hollow tube 100 as shown in FIG. 1A. As can be seen, the connector 102 extends around the periphery of the permanent umbilical hollow tube 100. In an alternative embodiment, the connector 102 extends only around a portion of the periphery of the permanent umbilical hollow tube 100. For example, the connector 102 may occupy two quadrants rather than all four quadrants of the permanent umbilical hollow tube 100. In that instance, the valve 104 may be shaped to extend into the areas not filled by the connector 102. Further, the connector 102 may extend in a circular, or semi-circular, configuration around the periphery of inside wall of the permanent umbilical hollow tube 100, but may extend inwardly in a different shape to operably connect to the valve 104. For example, the valve 104 may have a square shaped configuration. Accordingly, the connector 102 may extend inwardly to form an inner square to operably connect to the valve 104. A variety of shapes may be utilized for the configurations of the connector 102 and the valve 104.

In one embodiment, the permanent umbilical hollow tube 100 is non-absorbable and sterile. For example, the permanent umbilical hollow tube 100 may be made from a non-absorbable rigid, semi-rigid, pliable, expandable or soft plastic material such as an ethylene vinyl acetate copolymer, Gortex, Silicon, or other non-absorbable synthetic material. The permanent umbilical hollow tube 100 may also be made from a variety of plastics, polymers, composites, silicone, polyurethane, a combination thereof, or other non-absorbable synthetic material. The permanent umbilical hollow tube 100 may be made from metals such as titanium. In one embodiment, the permanent umbilical hollow tube 100 is made from a material that has sufficient flexibility to withstand insertion of a device through it such as a surgical device, drug delivery device, imaging device, Global Positioning System ("GPS") device, homing device, microchip, or the like. The material of a specific permanent umbilical hollow tube 100 may be selected for a particular patient. For example, if a medical determination is made prior to birth that a particular fetus is likely to be premature or have a specific medical problem, a permanent umbilical hollow tube 100 with specific properties, as opposed to permanent umbilical hollow tube 100 made from a generic material for individuals without complications, may be selected to allow for further diagnosis or treatment of that particular individual. Depending on the use, the permanent umbilical hollow tube 100 may have various properties of elasticity, tensile strength, permeability, durability, porousness, temperature stability (e.g., the permanent umbilical hollow tube 100 may be made from a material to withstand up to 106 degrees Fahrenheit if an individual has a fever or a higher temperature to withstand a great deal of heat generated from a device, e.g., a laser, that is pointed through or placed in the permanent umbilical hollow tube 100).

In one embodiment, the materials utilized in the permanent umbilical hollow tube 100, the connector 102, and the valve 104 are non-toxic, non-carcinogenic, and safe for implantation in a human being. Further, if plastic materials are utilized, the plastic materials will be non-latex and hypoallergenic. The materials are selected to not diminish substantially in structure or shape, i.e., rigidity, over time unless there is a mechanical alteration. Further, the materials are selected so not to be incorporated into the body on a molecular level. In one embodiment, the permanent umbilical hollow tube 100, the connector 102, and the valve 104 are sterile and coated with an antimicrobial, antibacterial, and/or antiviral coating to help reduce the spread of infection.

FIG. 1C illustrates a plan view of the permanent umbilical hollow tube 100 as shown in FIG. 1A. As an example, the permanent umbilical hollow tube 100 may have dimensions of a diameter of approximately one millimeter to six centimeters and a length of approximately one centimeter to three centimeters. However, the dimensions depend on the size of the fetus, umbilical vein, and umbilical arteries, which may largely vary depending on the newborn.

FIG. 2 illustrates a magnified view of the valve 104. In one embodiment, the valve 104 includes a top member 202 and a bottom member 204 that close the opening to the permanent umbilical hollow tube 100. As a result, the contents of the permanent umbilical hollow tube 100 may be effectively stored. To obtain access to the permanent umbilical hollow tube 100, pressure may be exerted on the top member 202, which thereby exerts pressure on the bottom member 204. In one embodiment, the top member 202 and the bottom member 204 are made from flexible materials so that these members bend upon receiving pressure to provide access to the permanent umbilical hollow tube 100. In another embodiment, the top member 202 and the bottom member 204 are each operably connected to the inner wall of the connector 102 via a hinge so that the members can provide access to the permanent umbilical hollow tube 100 upon receiving pressure and close off access to the permanent umbilical hollow tube 100 upon removal of that pressure. In yet another embodiment, a rubber stop cock may be utilized for the valve 104. The stop cock is made from a material that is flexible and pliable so as to allow for the penetration of a syringe and the ability to dilate for the insertion of a larger medical device such as a medical imaging device or other surgical device. The stop cock may also be designed to swing open on a one sided hinge internally to allow for it to open completely internally and allow for the insertion of a larger device. In another embodiment, multiple valves may be utilized. A variety of valve configurations may be utilized. Further, a valve configuration may be operably connected to the permanent umbilical hollow tube 100 rather than to the connector 102.

In one embodiment, the valve 104 is configured to allow only outward-to-inward access to the permanent umbilical hollow tube 100. Accordingly, the bottom end of the permanent umbilical hollow tube 100, as shown in FIG. 1A, may be positioned in the umbilical vein or one of the umbilical arteries. Further, the top end of the permanent umbilical hollow tube 100, as shown in FIG. 1A, may be positioned under the skin of the umbilicus so that access to the permanent umbilical hollow tube 100 does not necessitate a deep incision.

Various configurations may be utilized to access the inner wall of the permanent hollow tube 100. For example, the first end may have a barrier and/or the second end may have a barrier. The one or more barriers may be made from a penetrable material so that a syringe or other surgical device may be inserted through the barrier. The one or more barriers may alternatively or additionally be made from an expandable material to allow another surgical device to be inserted through the permanent hollow tube 100. By having both barriers, fibrous material may be prevented from building up inside the permanent hollow tube 100. However, the permanent hollow tube 100 may have one open end and a barrier on the other side or two open ends.

Figure 3:
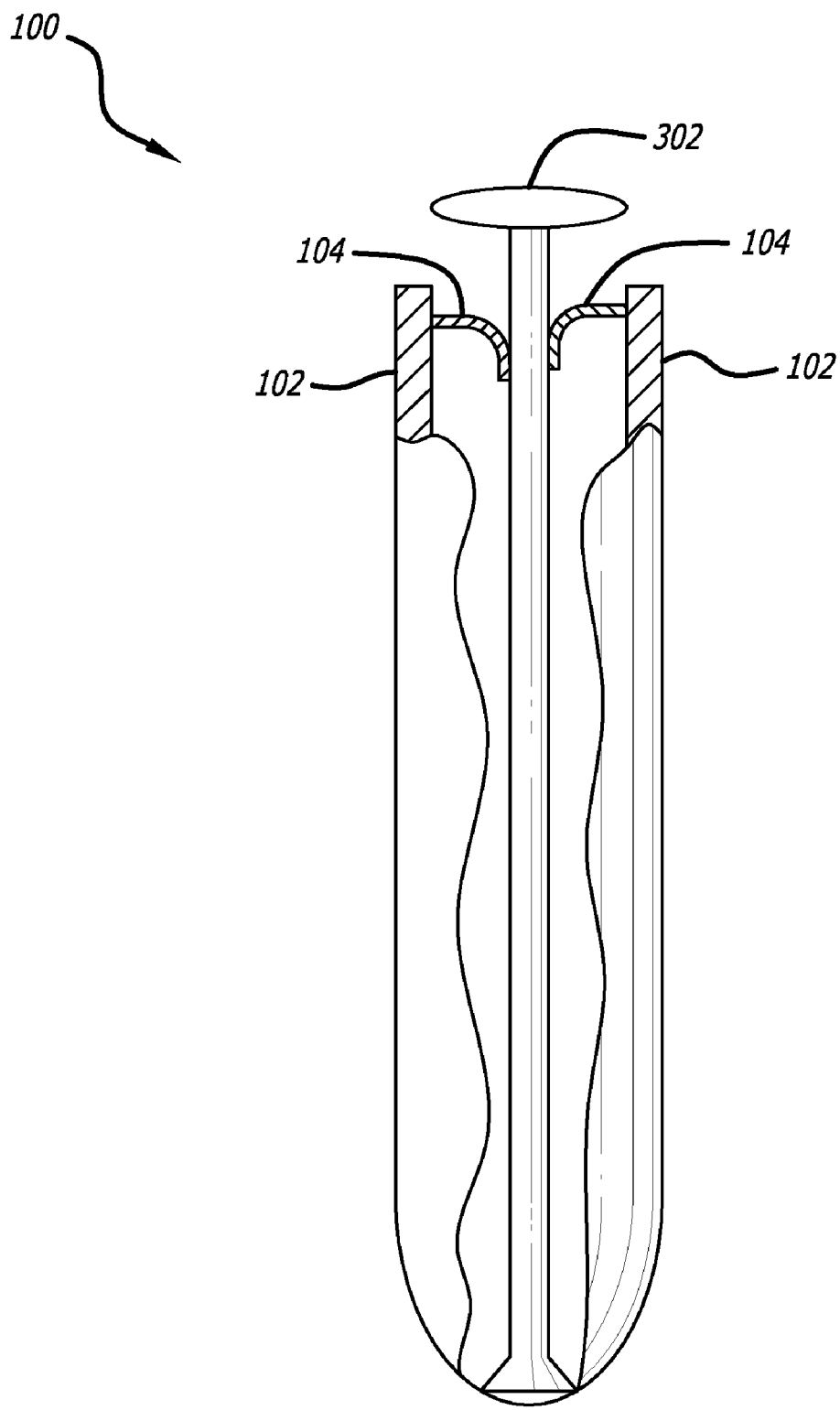
FIG. 3 illustrates a guiding rod that may be utilized for positioning of the permanent umbilical hollow tube, as shown in FIG. 1A, in the umbilical vein or one of the umbilical arteries.

FIG. 3 illustrates a guiding rod 302 that may be utilized for positioning of the permanent umbilical hollow tube 100, as shown in FIG. 1A, in the umbilical vein or one of the umbilical arteries. The guiding rod 302 is pushed through the valve 104 to open the valve 104. The end of the guiding rod 302 that contacts the bottom of the permanent umbilical hollow tube 100 may have a variety of shapes to effectively move the permanent umbilical hollow tube 100. For example, the end of the guiding rod 302 may have a flat configuration, a rounded configuration, etc. As the bottom of the permanent umbilical hollow tube 100 may have a variety of shapes, the most effective shape of end of the guiding rod 302 depends on the shape of bottom of the permanent umbilical hollow tube 100. Further the top end of the guiding rod 302 may have a handle, a flat surface, a round surface, etc. that may be utilized to push the guiding rod 302 through the valve 104 to open the valve and position the permanent umbilical hollow tube 100, and pull the guiding rod 302 out of the permanent umbilical hollow tube 100 through the valve 104 so that the valve 104 closes access to the permanent umbilical hollow tube 100. A variety of devices other than the guiding rod 302 may be utilized to access the permanent umbilical hollow tube 100 in a manner similar to that of the guiding rod 302. For example, a variety of devices, as described above, may be inserted into the permanent umbilical hollow tube 100 after the permanent umbilical hollow tube 100 is positioned into the umbilical vein or one of the umbilical arteries.

In an alternative embodiment, a guiding wire may be utilized instead of a the guiding rod 302. In yet another embodiment, any guiding member may be utilized for placement of the permanent umbilical hollow tube 100. The guiding member may be the guiding rod 302, a guiding wire, or any other member that assists in the positioning of the permanent umbilical hollow tube 100. In another embodiment, no guiding rod is utilized. For example, one or more hands may be utilized in the positioning of the permanent umbilical hollow tube 100. In yet another embodiment, air may be injected into the permanent umbilical hollow tube 100 to expand and extend the permanent umbilical hollow tube 100 to its maximum length to occupy the vein or artery.

Figure 4:
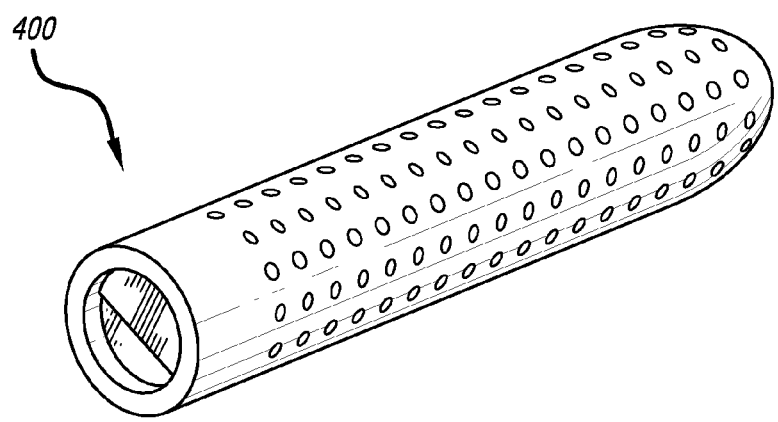
FIG. 4 illustrates the permanent umbilical hollow tube, as shown in FIG. 1A, with a plurality of microfenestrations.

In an alternative embodiment, the permanent umbilical hollow tube 100 may have a plurality of microfenestrations, i.e., holes. FIG. 4 illustrates the permanent umbilical hollow tube 100, as shown in FIG. 1A, with a plurality of microfenestrations 402. In one configuration, the plurality of microfenestrations 402 may be smaller than the diameter of devices that are to be inserted into the permanent umbilical hollow tube 100. Further, the plurality of microfenestrations 402 may be large enough to act as a drug or fluid/gel delivery system and/or to allow for the penetration of various substances into the surrounding mucosa or tissue in the abdomen. In one embodiment, each of the plurality of microfenestrations 402 is of the same dimensions. In an alternative embodiment, each of the plurality of microfenestrations 402 is of a different dimension.

Figure 5:
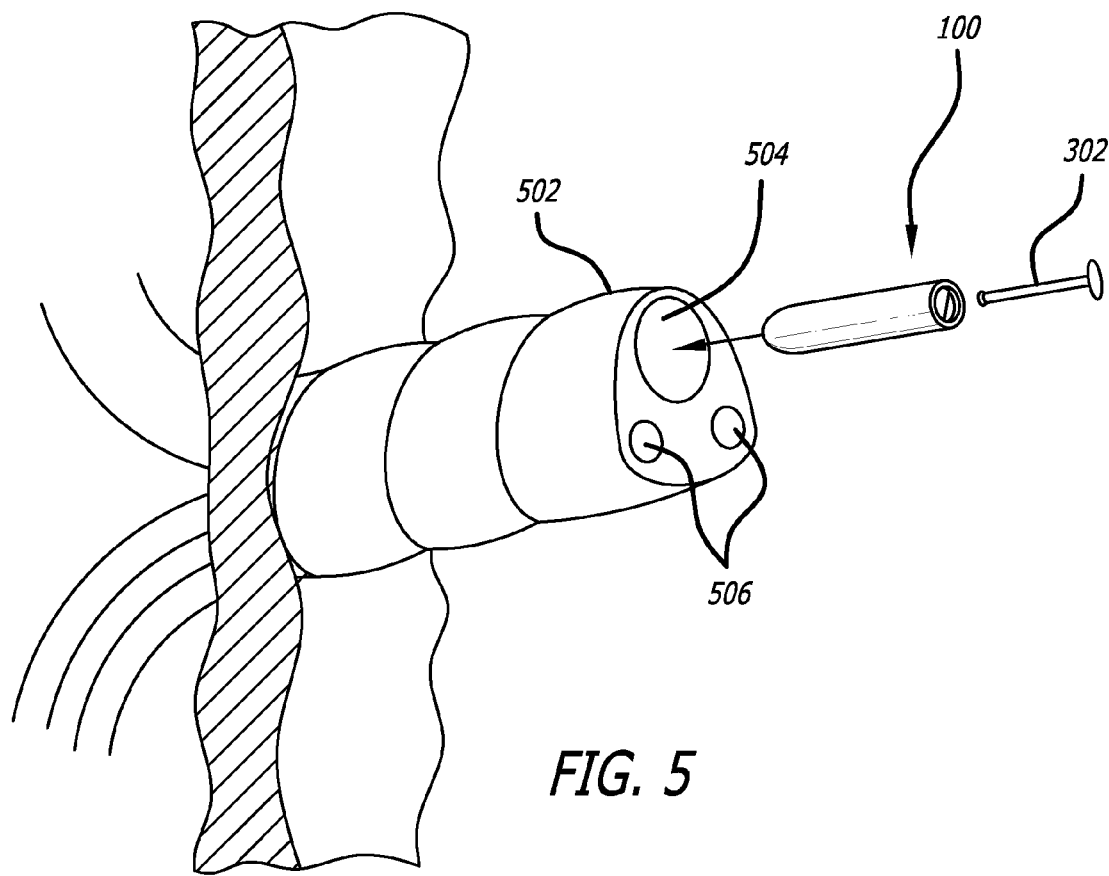
FIG. 5 illustrates the permanent umbilical hollow tube being inserted into an umbilical vessel in the umbilical cord.

FIG. 5 illustrates the permanent umbilical hollow tube 100 being inserted into an umbilical vessel in the umbilical cord 502. The umbilical vessel may be the umbilical vein 504 or one of the umbilical arteries 506. The guiding rod 302, as shown in FIG. 3, may be utilized to insert the permanent umbilical hollow tube 100 into the umbilical vessel. The guiding rod 302 is then removed. The umbilical cord 502 is then clamped after the birth of the newborn.

Figure 6:
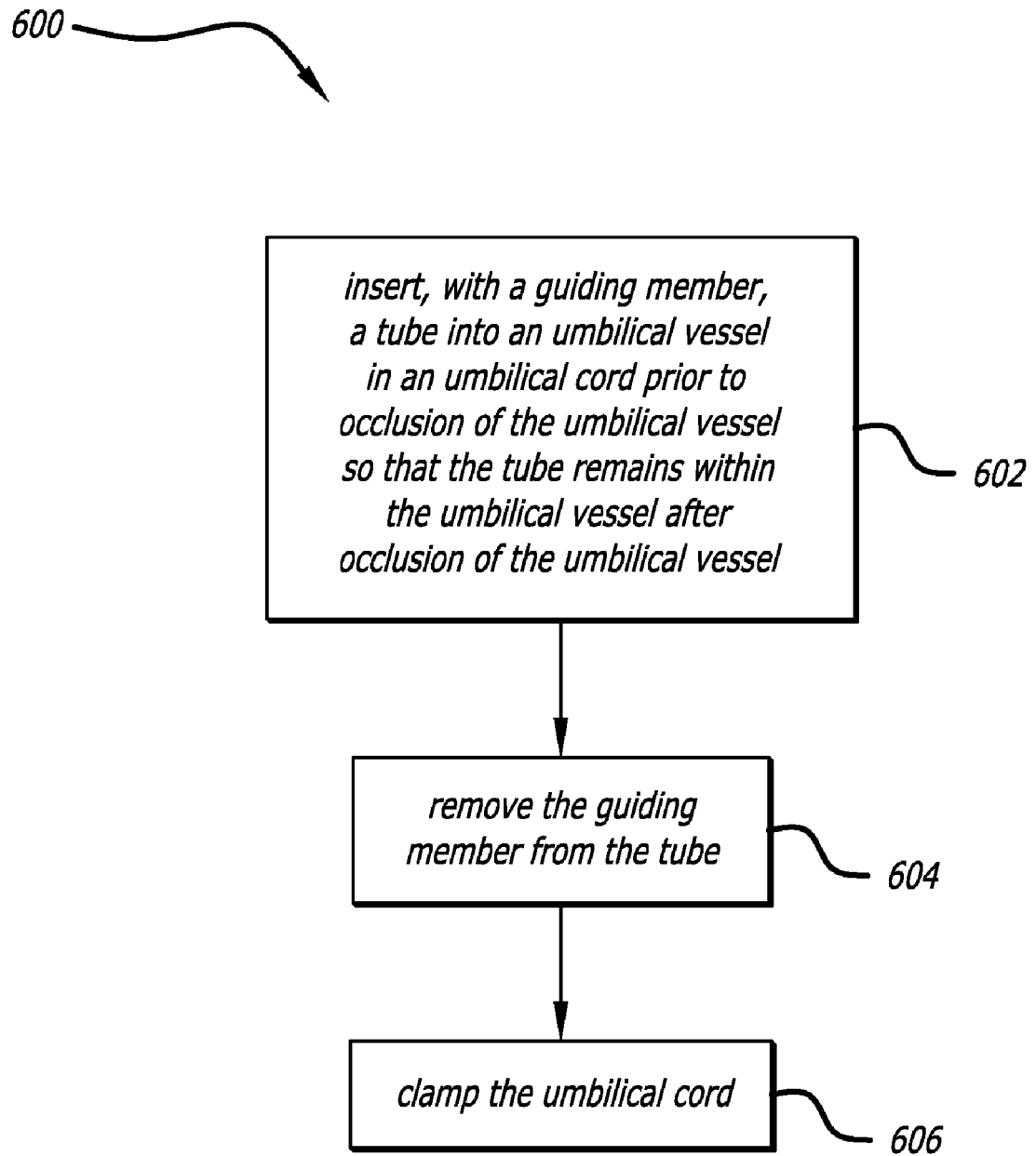
FIG. 6 illustrates a process that may be utilized for insertion of the permanent umbilical hollow tube.

FIG. 6 illustrates a process 600 that may be utilized for insertion of the permanent umbilical hollow tube 100. At a process block 602, the process 600 inserts, with a guiding member, a tube into an umbilical vessel in an umbilical cord prior to occlusion of the umbilical vessel so that the tube remains within the umbilical vessel after occlusion of the umbilical vessel. In one embodiment, the insertion of the tube is effectuated into an umbilical vessel in the body. Further, at a process block 604, the process 600 removes the guiding member from the tube. Finally, at a process block 606, the process 600 clamps the umbilical cord. In one embodiment, the clamping of the umbilical cord occurs at the umbilicus. After the occlusion of the umbilical vessel in the umbilical cord, the clamp eventually falls off.

Once the permanent umbilical hollow tube 100 is permanently positioned within the body, an incision can be made at a later time, even when the individual is an adult, to obtain access to the tube. The permanent umbilical hollow tube 100 can be utilized for a number of reasons. A homing device can be placed and stored in the permanent umbilical hollow tube 100 at time of insertion, or later through incision, so that a newborn can be tracked by the family. The homing device can also be inserted into prisoners for tacking purposes. Alternatively, the hollow tube can be utilized for medical purposes to insert medicine at a future time with less of an incision than would normally be needed if the permanent umbilical hollow tube 100 was not present. For example, the permanent umbilical hollow tube 100 may also be utilized as a site for dialysis in the future if ever necessary, access to abdominal organs or vessels, or access to the bladder for catheterization of urine. Processes such as hemodialysis, peritoneal dialysis, or other mechanism of filtration or drainage of blood or bodily fluids may be utilized.

Although the permanent umbilical hollow tube 100 is described above with a tubular configuration, a variety of other configurations and shapes may be utilized. For example, the valve 104 may be positioned on the side of the permanent umbilical hollow tube 100. Further, a subset, or all, of the umbilical arteries and the umbilical vein may be cannulated. In other words, multiple permanent umbilical hollow tubes 100 may be utilized. For example, multiple permanent umbilical hollow tubes 100 may be helpful if large doses of medicine may need to be delivered in an individual. The multiple permanent umbilical hollow tubes 100 may differ in size as the sizes of the umbilical vessels in the individual may differ.

It is understood that the method and apparatus described herein may also be applied in other types of methods and apparatuses. Those skilled in the art will appreciate that the various adaptations and modifications of the embodiments of this method and apparatus may be configured without departing from the scope and spirit of the present method and system. Therefore, it is to be understood that, within the scope of the appended claims, the present method and apparatus may be practiced other than as specifically described herein.

We claim:

1. A method of permanently placing a tube within an umbilical vessel of a newborn, the method comprising:
    inserting, with a guiding member, a tube into an umbilical vessel in an umbilical cord prior to occlusion of the umbilical vessel,
        wherein the tube is configured to have dimensions so that the tube remains in a fixed position within the umbilical vessel of an umbilical cord both prior to and after the occlusion of the umbilical vessel;
        the tube having a first end and a second end, the second end being closed; and
        a valve operably connected to the first end of the tube and configured to provide access to the interior of the tube to the guiding member;
        wherein the tube is impermeable;
    removing the guiding member from the tube; and
    clamping the umbilical cord,
    whereby the tube is permanently placed within the umbilical vessel of the newborn.

2. The method of claim 1, wherein the umbilical vessel is an umbilical vein.

3. The method of claim 1, wherein the umbilical vessel is an umbilical artery.

4. The method of claim 1, wherein the guiding member is inserted into the tube through the first end of the tube.

5. The method of claim 1, wherein the newborn is a human.

6. The method of claim 1, wherein the valve is also configured to provide access to the interior of the tube to a surgical device.

7. The method of claim 1, wherein the valve is also configured to provide access to the interior of the tube to a drug delivery device.

8. A method of permanently placing a tube within an umbilical vessel of a newborn, the method comprising:
    inserting the tube into the umbilical vessel in an umbilical cord prior to occlusion of the umbilical vessel so that the tube remains within the umbilical vessel after the occlusion of the umbilical vessel,
        wherein the tube is configured to have dimensions so that the tube remains in a fixed position within the umbilical vessel of an umbilical cord both prior to and after the occlusion of the umbilical vessel;
        the tube having a first end and a second end, the second end being closed; and
        a valve operably connected to the first end of the tube;
        wherein the tube is impermeable; and
    clamping the umbilical cord,
    whereby the tube is permanently placed within the umbilical vessel of the newborn.

9. The method of claim 8, wherein the valve is also configured to provide access to the interior of the tube to a device selected from the group consisting of an imaging device, a Global Positioning System device, a homing device, and a microchip.

10. The method of claim 8, wherein the umbilical vessel is an umbilical vein.

11. The method of claim 8, wherein the umbilical vessel is an umbilical artery.

12. The method of claim 8, wherein the valve is also configured to provide access to the interior of the tube to a surgical device.

13. The method of claim 8, wherein the valve is also configured to provide access to the interior of the tube to a drug delivery device.

14. The method of claim 8, wherein the valve is also configured to provide access to the interior of the tube to a device selected from the group consisting of an imaging device, a Global Positioning System device, a homing device, and a microchip.

15. The method of claim 8, wherein the newborn is a human.

* * * * *